US008608695B2

(12) United States Patent
Hauri et al.

(10) Patent No.: US 8,608,695 B2
(45) **Date of Patent: *Dec. 17, 2013**

(54) SAFETY NEEDLE ASSEMBLY

(75) Inventors: Marius Hauri, Westmoreland, NH (US); Frank Blinkhorn, Keene, NH (US); David MacLean, Swanzey, NH (US); Lawrence P. Hudon, Hinsdale, NH (US); Robert Simas, Jr., Keene, NH (US); Troy M. Derby, Stoddard, NH (US)

(73) Assignee: Smiths Medical ASD, Inc., Rockland, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/413,103

(22) Filed: Mar. 6, 2012

(65) Prior Publication Data

US 2012/0172810 A1 Jul. 5, 2012

Related U.S. Application Data

(60) Division of application No. 10/832,339, filed on Apr. 27, 2004, now Pat. No. 8,152,761, which is a continuation-in-part of application No. 10/665,514, filed on Sep. 22, 2003, now Pat. No. 8,251,961.

(51) Int. Cl.
*A61M 5/00* (2006.01)

(52) U.S. Cl.
USPC ............................ 604/110; 604/263; 604/192

(58) Field of Classification Search
USPC ......... 604/110, 111, 192, 198, 240–243, 263, 604/164.08; 128/919
See application file for complete search history.

(56) References Cited

U.S. PATENT DOCUMENTS

| | | | |
|---|---|---|---|
| 2,693,183 A | 11/1954 | Lockhart | |
| 4,664,259 A | 5/1987 | Landis | |
| 4,982,842 A | 1/1991 | Hollister | |
| 5,037,401 A | 8/1991 | DeCamp | |
| 5,139,489 A | 8/1992 | Hollister | |
| 5,154,285 A | 10/1992 | Hollister | |
| 5,188,611 A | 2/1993 | Orgain | |
| 5,232,454 A | 8/1993 | Hollister | |
| 5,277,311 A | 1/1994 | Hollister | |
| 5,445,619 A | 8/1995 | Burns | |
| 5,490,841 A | 2/1996 | Landis | |
| 5,509,907 A | 4/1996 | Bevilacqua | |
| 5,584,816 A | 12/1996 | Gyure et al. | |
| 5,599,313 A | 2/1997 | Gyure et al. | |
| 5,599,318 A | 2/1997 | Sweeney et al. | |
| 5,615,771 A * | 4/1997 | Hollister | 206/365 |
| 5,632,732 A | 5/1997 | Szabo et al. | |
| 5,643,219 A | 7/1997 | Burns | |
| 5,662,617 A | 9/1997 | Odell et al. | |

(Continued)

*Primary Examiner* — Kevin C Sirmons
*Assistant Examiner* — Laura Schell
(74) *Attorney, Agent, or Firm* — Louis Woo

(57) ABSTRACT

A safety needle assembly has a collar or ring that is rotatably mounted to a needle hub. The needle assembly may be connected to a syringe by the user grasping the needle hub in first and second embodiments, or turning of the needle sheath in other embodiments. The collar of the needle assembly may be rotated by turning the needle sheath. The needle hub may also interact with the collar by rotating the needle sheath. Mechanisms are provided at both the collar and the housing so that once the contaminated needle is covered, the needle assembly may be removed from the syringe for disposal by rotating the needle housing.

11 Claims, 9 Drawing Sheets

(56) References Cited

U.S. PATENT DOCUMENTS

| | | | |
|---|---|---|---|
| 5,665,075 | A | 9/1997 | Gyure et al. |
| 5,669,889 | A | 9/1997 | Gyure et al. |
| 5,681,295 | A | 10/1997 | Gyure et al. |
| 5,697,908 | A | 12/1997 | Imbert et al. |
| 5,733,265 | A | 3/1998 | Bachman et al. |
| 5,868,716 | A | 2/1999 | Sweeney et al. |
| 5,891,103 | A | 4/1999 | Burns |
| 5,913,846 | A | 6/1999 | Szabo |
| 5,919,165 | A | 7/1999 | Benson |
| 5,993,426 | A | 11/1999 | Hollister |
| RE37,110 | E | 3/2001 | Hollister |
| RE37,252 | E | 7/2001 | Hollister |
| 6,328,713 | B1 | 12/2001 | Hollister |
| 6,334,857 | B1 | 1/2002 | Hollister |
| 6,440,104 | B1 | 8/2002 | Newby et al. |
| 6,582,397 | B2 | 6/2003 | Alesi et al. |
| 6,719,737 | B2 | 4/2004 | Kobayashi |
| 7,014,622 | B1 | 3/2006 | Pressly et al. |
| 7,090,656 | B1 | 8/2006 | Botich et al. |
| 7,156,825 | B2 | 1/2007 | Hudon |
| 2002/0010433 | A1 | 1/2002 | Johnson et al. |
| 2002/0161336 | A1 | 10/2002 | Crawford et al. |
| 2003/0078548 | A1 | 4/2003 | Kobayashi |

* cited by examiner 2
76
76
8
74
12
92
70
6
42
4
28

76
10
8
42
24
92
12
38
26
42
28
62
6
68
22

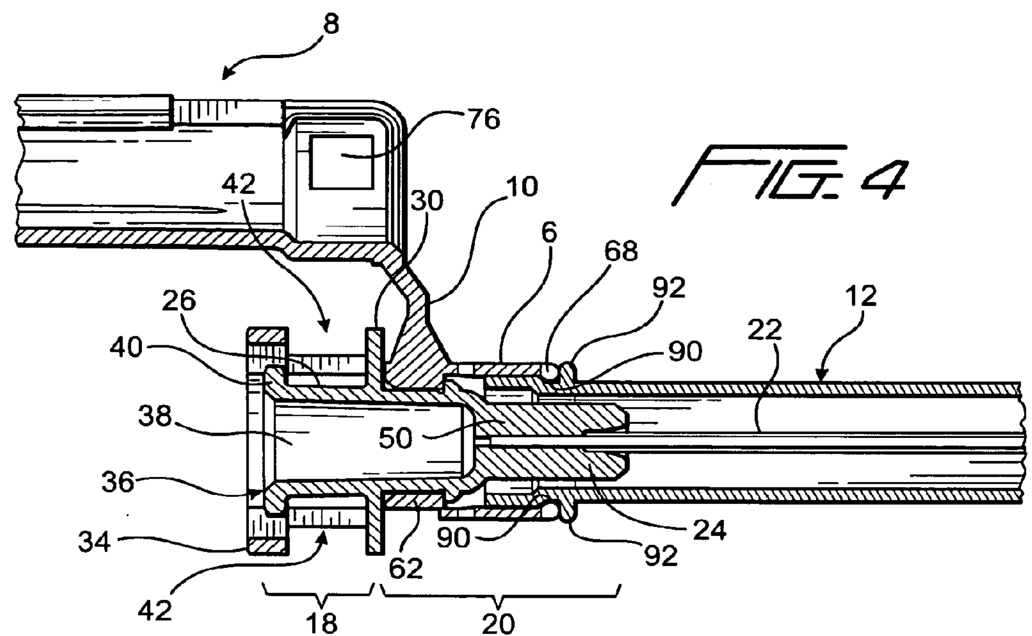
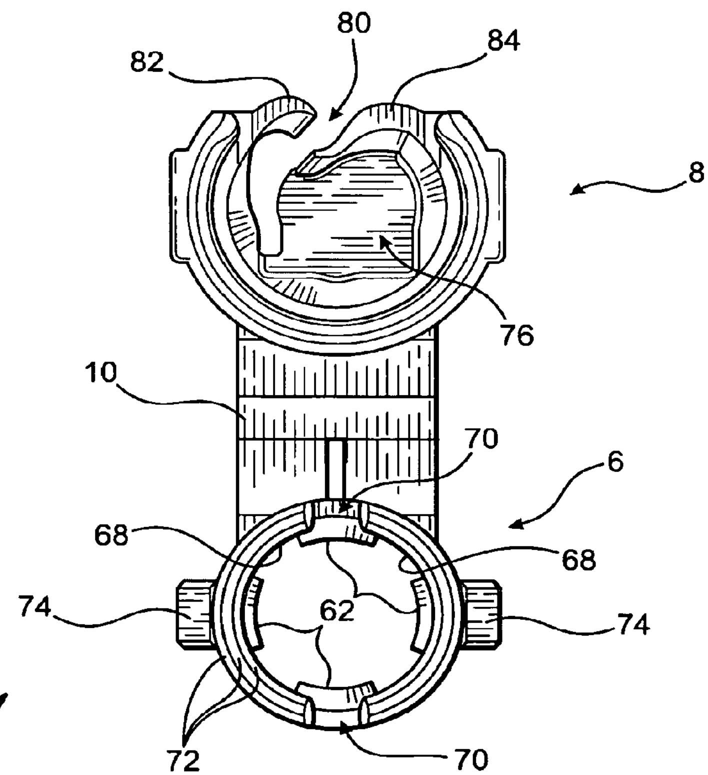
FIG. 11

168
14
170B
170A
10
160A
150A
158
8
164
148
152
154
162
166
52
128
154
160B
156
162
130
166
14
12
6
150B
40
4

SAFETY NEEDLE ASSEMBLY

This application is a divisional of application Ser. No. 10/832,339 filed Apr. 27, 2004, now U.S. Pat. No. 8,152,761 which in turn is a continuation-in-part of application Ser. No. 10/665,514 filed Sep. 22, 2003, now U.S. Pat. No. 8,251,961.

CROSS REFERENCE TO RELATED APPLICATIONS

The instant invention is related to the invention disclosed in application Ser. No. 10/649,837 entitled "Needle Protection Assembly" filed on Aug. 27, 2003. The disclosure of the related application is incorporated by reference to this application.

FIELD OF THE INVENTION

The present invention relates to needles and more particularly a safety needle assembly in which the needle sheath for protecting the needle prior to use is attached to a collar rotatably mounted about the needle hub of the needle assembly.

BACKGROUND OF THE INVENTION

There are a number of needle protection devices disclosed in the prior art. Among them are a number of patents assigned to the same assignee as the instant invention. Without limitations, some of those patents are: U.S. Pat. Nos. 4,982,842; 5,139,489; 5,154,285; 5,232,454; 5,277,311; 5,993,426; 6,328,713; 6,334,857; RE 37,110 and RE 37,252. Some other patents that describe needle protection devices, or parts thereof, include U.S. Pat. Nos. 4,664,259; 5,037,401; 5,171,303; 5,188,611; 5,490,841; 5,509,907; 5,584,816; 5,599,313; 5,599,318; 5,632,732; 5,643,219; 5,662,617; 5,665,075; 5,669,889; 5,681,295; 5,697,908; 5,733,265; 5,868,716; 5,891,103; 5,913,846; 5,919,165 and 6,440,104.

The needle protection assembly of the instant invention is made up of parts that are radically different from the prior art, as exemplified by the above-noted patents.

SUMMARY OF THE PRESENT INVENTION

The safety needle assembly of the instant invention is designed to enable a user to connect the needle hub to a medical device, such as for example a syringe, by grasping the needle hub proper, thereby ensuring a more secure fit to the syringe. Unlike the prior art needle assemblies, the sheath that covers the needle plays no part in the securing of the needle hub to the medical device.

The needle hub is especially designed to have a ring surrounding the luer end of the hub to allow a user to grasp this ring to couple the needle hub to the medical device. The ring is an integral part of the needle hub and it has a distal wall that extends orthogonally from a proximal portion of the main body of the hub, with the body of the ring extending rearward to cover the luer end of the needle hub that couples to a corresponding luer of the medical device. The circumferential side wall of the ring is spaced from the luer of the needle hub. The proximal end of the ring is open to allow the mating of the luer of the needle hub to the corresponding luer of the medical device. To enable the user to see the initial blood flash so as to determine whether the needle has correctly been inserted into the vein of a patient during blood drawing, windows are provided at the sidewall of the ring to allow the user to have a clear view of the luer body, and the luer end.

The needle hub has at its distal portion a number of flanges formed along a circumferential axis. The flanges are chamfered at their respective surfaces that face the needle extending from the distal end of the needle hub. The back surfaces of the flanges are flat for defining a space between the flanges and the distal wall of the ring circumferentially formed about the distal portion of the needle hub.

A collar to which a needle protection housing is attached is fitted to the space defined by the flanges and the distal wall of the ring on the needle hub. To facilitate the fitting, a number of internal protrusions or bosses are provided at the proximal end of the collar. The respective surfaces of the protrusions that come into contact with the flanges at the needle hub are also chamfered to facilitate the mating of the collar to the needle hub. The back end of the substantially rectangular protrusions are flat, so that once the collar is fitted to the needle hub, it could not be removed therefrom.

At the distal portion of the collar there is formed a circumferential internal rib. Slots are also provided at the distal portion of the collar to enable the flexing of the distal end of the collar for the insertion and removal of a needle sheath that removably couples thereto.

The collar has pivotally or hingedly attached thereto a housing which is pivotable to the direction along a longitudinal axis of the needle hub for covering the needle after use. Formed substantially along the length of the housing is an opening that is off centered. The opening is formed by two lips or flaps that extend substantially along the length of the housing, with the first or upper lip overlapping the second or lower lip. The respective lips each are angled toward the interior of the housing, but with varying angles along the lengths of the lips. As a consequence, when the housing is pivoted to cover a used or contaminated needle, the needle would enter into the housing guided by the lips at angles that ensure that it smoothly enters into the housing, thereby preventing flickering of any contaminated fluid that may have adhered to the needle. The lips, particularly the lower lip, are designed such that, once fully enters into the housing, the needle is prevented from escaping from the housing. For added safety, respective portions of a locking mechanism are provided at the base portion of the housing and the outer surface of the distal portion of the collar.

The needle sheath that covers the needle prior to use has a notch or groove formed circumferentially proximate to its open end. During manufacturing of the needle assembly, the needle sheath is placed or positioned over the needle and moved along the longitudinal axis of the device to mate with the distal portion of the collar mounted about the needle hub. With a predetermined force, the needle sheath is coupled to the collar, with the rib at the distal end of the collar fitting into the groove formed at the proximal end of the needle sheath.

To remove the safety needle assembly of the instant invention from the medical device, the user would grasp the ring of the needle hub and rotate the needle assembly in a rotational movement that is counter to the rotational movement used to couple the needle assembly to the medical device, if the coupling of the needle assembly to the medical device is via luer lock coupling. If it is a luer fit coupling, then the user would pull the needle assembly away from the medical device.

Other embodiments of the safety needle assembly of the instant invention enable a user to connect the needle hub to a medical device with or without grasping the needle hub proper.

A first alternative embodiment of the safety needle assembly of the instant invention has a needle sheath that has a base that is larger in diameter than the collar, so that the needle sheath may be slip fitted over the collar. The base of the needle sheath is provided with two opposed slots or keyways that, when the needle sheath is slip fitted over the collar, each of the slots would mate with a corresponding catch member formed at the outer wall of the collar. As a consequence, the collar is rotatable in unison with the needle sheath, when the needle sheath is rotated by a user. For this alternative embodiment, the needle hub is the same as in the earlier embodiment so that to connect and disconnect the needle assembly from the luer end of a syringe, a user would still need to grasp the needle hub.

Another alternative embodiment of the needle assembly of the instant invention has a needle sheath that has a proximal open end to which opposed keys or protuberances are provided to mate with keyways or slots formed at the distal portion of the collar. Thus, once the needle sheath is fitted to the collar, the collar is rotatable in unison with the needle sheath, when the user rotates the needle sheath. The collar of this embodiment also has a proximal portion at the end of which there is a flange. The needle hub of this embodiment is provided with a ring at the portion to which the collar is rotatably mounted. The ring has two end stops, along with at least one protuberance along the edge between the stops, for providing guidance to the rotational positioning of the collar relative to the needle hub. Once the collar is rotatably mounted about the needle hub, the flange at its proximal end would coact against the edge of the ring between the two end stops, so that the collar could be rotated between the two end stops 180°, with the protuberance possibly providing an indication for the user that the collar is at a midpoint between the two end stops relative to the needle hub. The midpoint positioning of the collar relative to the needle hub allows a user to align the bevel end of the needle away from the housing, so that the user could have a clear view of the bevel of the needle for insertion into the vein of a patient. With the end stops, the needle assembly of this embodiment may be connected to and disconnected from a syringe, respectively, by the user turning the needle sheath, prior to the needle being exposed, and turning the housing, after the needle sheath has been removed and after the housing has been pivoted to cover the contaminated needle.

Another embodiment of the safety needle assembly of the instant invention has the just mentioned needle sheath. But for this embodiment, the collar is designed to have a number of fingers extending at its proximal end and a number of catches or heads that extend from the internal pads of the collar that allow the collar to be rotatable about the needle hub. As before, the needle hub has two sets of orthogonal flanges extending from its body for defining a space or groove about which the pads of the collar are movably mounted. To connect the needle assembly of this embodiment to a syringe, a user would hold the needle sheath and push it forward toward the syringe so that some of the fingers extending from the proximal end of the collar come into contact with the aft set of flanges, or rather the edges thereof, of the needle hub, so that the needle hub is rotated, when the needle sheath is rotated, for mating the needle hub to the luer end of the syringe. To remove the needle assembly after use, assuming that the needle sheath has been removed and the contaminated needle is covered by the needle housing which had been pivoted to cover the same and lockingly retained to the collar, a user would pull the collar away from the syringe so that some of the heads of the internal pads of the collar come into contact with the fore flanges, or rather the edges of those flanges, so as to enable to the user to rotatably remove the needle hub from the syringe.

Yet another embodiment of the safety needle assembly of the instant invention has a needle sheath that has an enlarged proximal end dimensioned to slip fit over the needle collar. The enlarged proximal end of the needle sheath is designed to have a slot that mates with the portion of the living hinge that extends from the collar for connecting the needle protection housing. A pair of opposed spring arms are provided at the proximal end of the housing, so that when the needle sheath is slip fitted over the collar, those spring arms are pushed inwardly toward the interior of the collar, which is rotatably mounted about a portion of the needle hub defined by two sets of spaced flanges. The space or groove on the needle hub of this embodiment of the needle assembly has two flat sections that enable the spring arms to press against the needle hub in a rest position, when the needle sheath is fitted over the collar. Thus, before the needle sheath is removed from the collar, a user can readily connect the needle hub, which rotates in unison with the collar, which in turn rotates in unison with the needle sheath, to the luer end of a syringe. The housing for this alternative embodiment of the needle assembly has a pair of legs or protrusions extending at its open end so that, when the housing is pivoted to cover a contaminated needle, the protrusions would bias against the spring arms at the collar to thereby press those spring arms against the flat sections of the needle hub about which the collar is mounted. As a consequence, by rotating the housing, the needle hub likewise is rotated and therefore is removable from a syringe.

Yet another embodiment of the needle assembly of the instant invention is designed to include a collar that has a proximal portion that rotatably mounts about a needle hub and a number of internal spring fingers that extend from the proximal portion of the collar to the distal portion of the collar. The needle hub of this embodiment of the needle assembly is designed to be similar to that of the incorporated by reference '837 application in that it has a number of arms formed coplanarly at the distal portion of the needle hub. Once the collar is rotatably mounted about the proximal portion of the needle hub, with the insertion of the needle sheath into the collar, the internal spring arms of the collar are biased inwards to rest within spaces defined by adjacent pairs of the coplanar arms. As a consequence, the needle hub rotates in unison with the collar and the needle sheath, which is designed to press-fit into the collar, is able to rotate the collar by its tight fit thereto. The needle assembly of this embodiment of the instant invention can therefore be readily connected to a syringe. The housing of this embodiment of the needle assembly is designed to have a leg extending from its open end to bias one of the spring arms inward, when the housing is pivoted to cover the exposed needle. With the spring arm biased inward to be positioned between a space defined by adjacent coplanar arms at the distal portion of the needle hub, a user can rotate the housing to cause the needle hub to likewise rotate, thereby removing the needle hub from the syringe.

BRIEF DESCRIPTION OF THE FIGURES

The present invention will become apparent and the invention itself will be best understood with reference to the following description of an embodiment of the present invention taken in conjunction with the accompanying drawings, wherein:

FIG. 2 is a perspective view showing the various components of the safety needle assembly of FIG. 1 and a medical device such as a conventional needle syringe to which the safety needle assembly of the instant invention is used with;

FIG. 4 is a cross-sectional view of the safety needle assembly of the instant invention;

FIG. 11 is a plan view of the needle protection housing and the collar component of the safety needle assembly of the instant invention;

FIG. 14 is a perspective view of an alternative embodiment of the needle assembly of the instant invention;

DETAILED DESCRIPTION OF THE INVENTION

Figure 1:
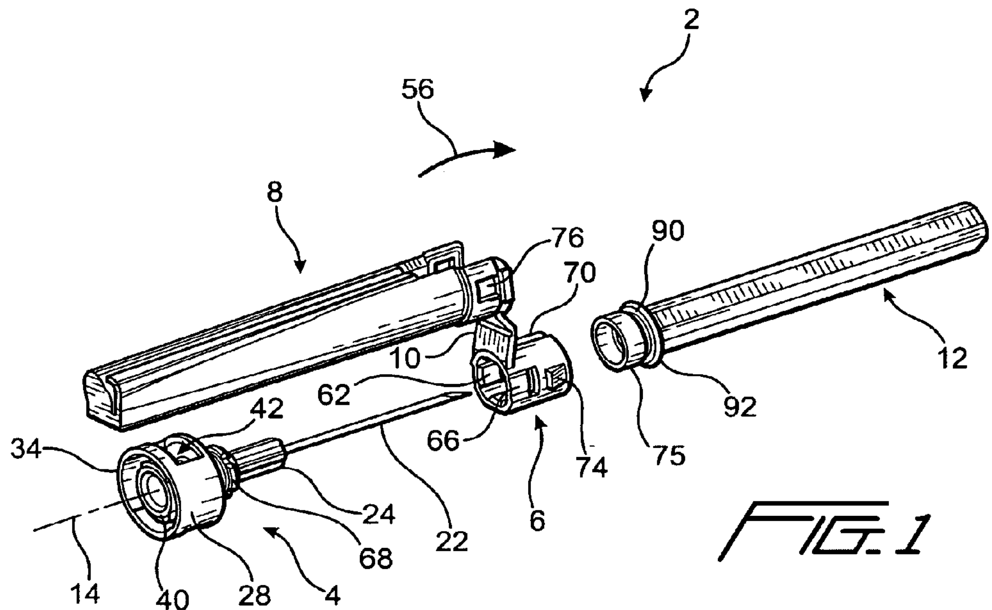
FIG. 1 is a perspective view showing the different component parts of the safety needle assembly of the instant invention.

With reference to FIG. 1, the safety needle assembly 2 of the instant invention is shown to comprise four major components, namely a needle hub 4, a collar 6, a needle protection housing 8 attached to the collar 6 via a living hinge 10, and a needle sheath 12. As shown, needle hub 4, collar 6 and needle sheath 12 are in alignment along a longitudinal axis 14. The exposed components of the safety needle assembly of the instant invention are further shown in FIG. 2 to be in alignment with a conventional syringe 16 with a luer lock receptacle end that mates with needle hub 4. An assembled safety needle assembly of the instant invention is shown in perspective view in FIG. 3 and in cross-sectional views in FIGS. 4 and 5.

Figure 5:
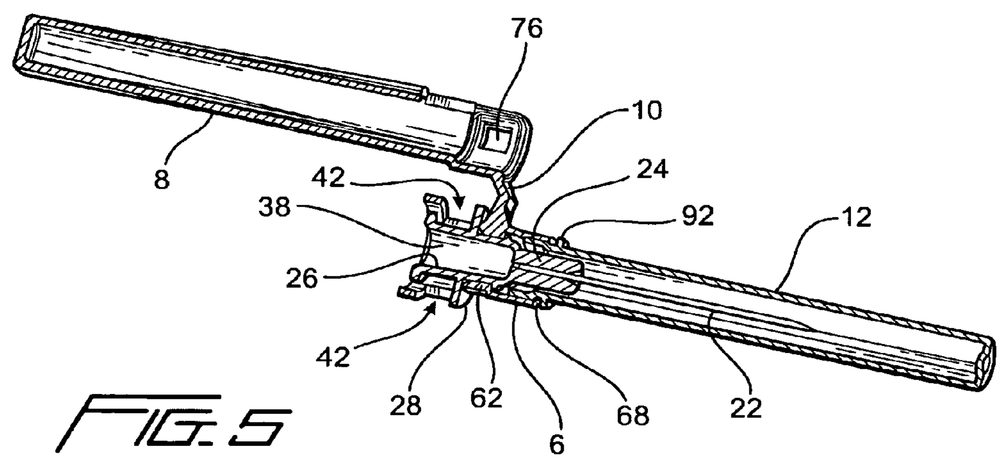
FIG. 5 is a perspective cross-sectional view of the needle assembly of the instant invention.
Figure 6:
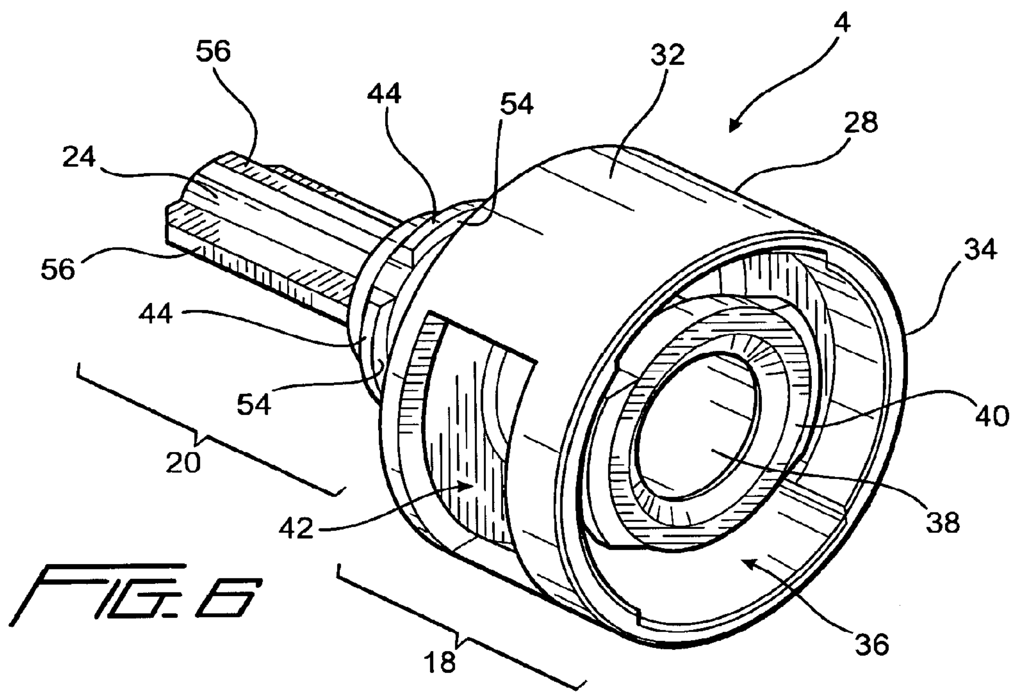
FIG. 6 is a perspective view of the needle hub of the safety needle assembly of the instant invention as viewed from its proximal end.
Figure 7:
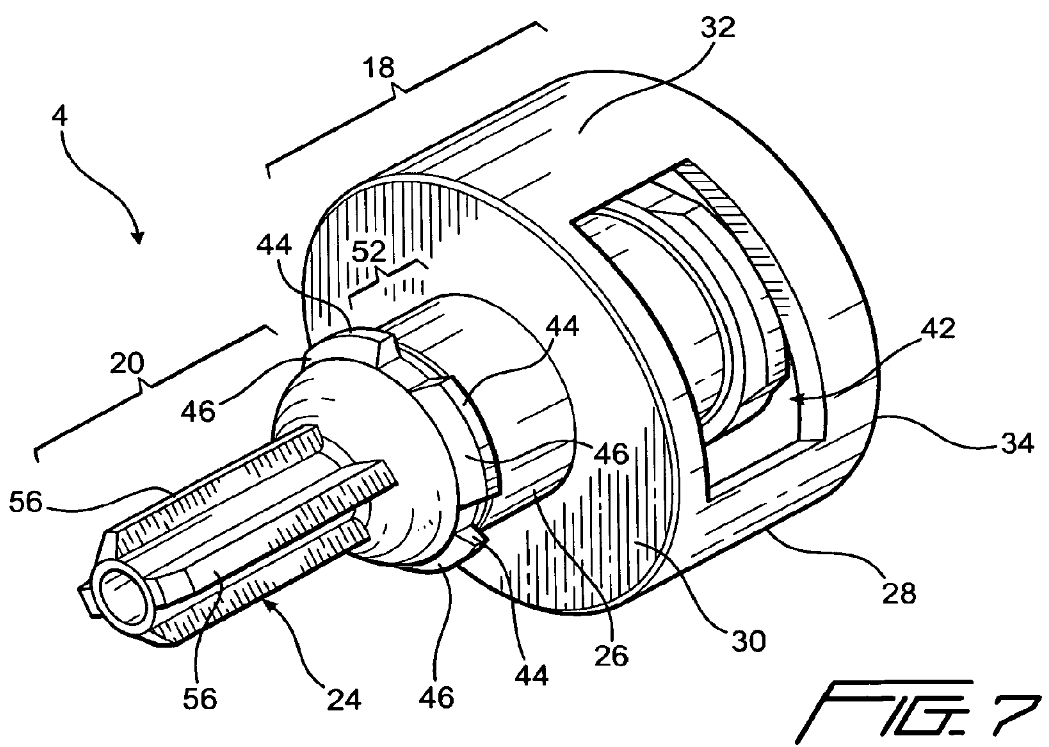
FIG. 7 is a perspective view of the needle hub of the instant invention safety needle assembly viewed from its distal end.
Figure 8:
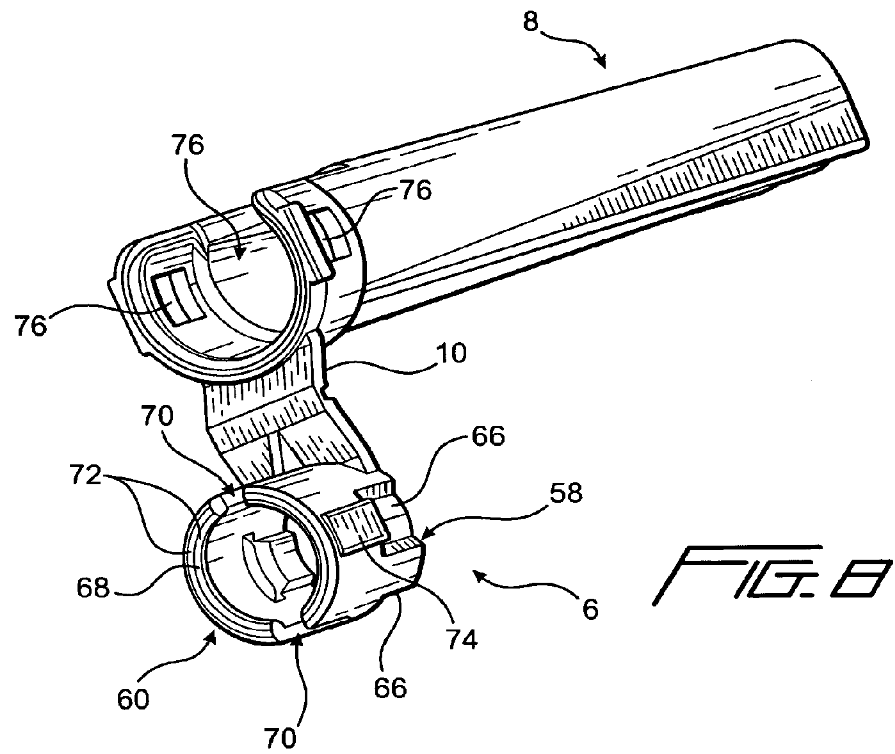
FIG. 8 is a perspective view of the needle protection housing and the collar to which it is attached.
Figure 9:
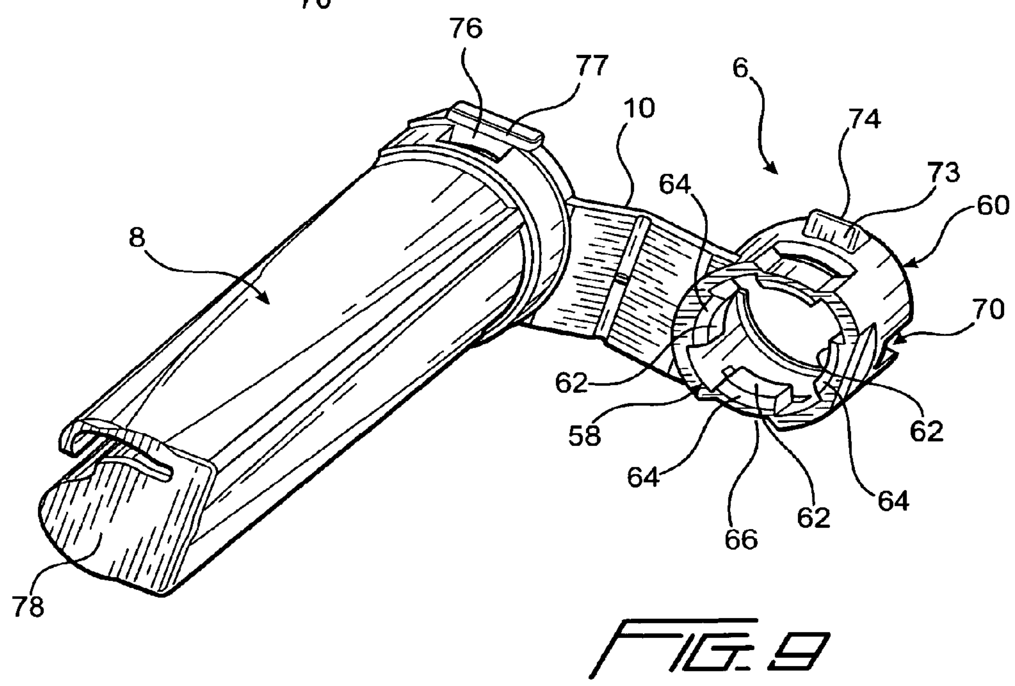
FIG. 9 is another perspective view of the FIG. 8 needle protection housing and collar.

With reference to FIGS. 1-5 and further with reference to FIGS. 6 and 7, needle hub 4 is shown to have a proximal portion 18 and a distal portion 20. For the sake of clarity, a needle 22 that fixedly extends from extension 24 of needle hub 4 is not shown in FIGS. 6 and 7. Further, it should be appreciated that proximal portion 18 and distal portion 20 of needle hub 4 do not have any actual line of demarcation, and are shown as such in FIGS. 4, 6 and 7 solely for the convenience of the reader.

As best shown in FIG. 6 and the cross-sectional views of FIGS. 4 and 5, needle hub 4 comprises a main body portion 26 that includes the base of needle hub 4. A ring 28 circumferentially surrounds the proximal portion of needle hub 4 in spaced relationship to main body portion 26. As shown, ring 28 is a part of needle hub 4 and is an integral part of main body portion 26 by means of a distal wall or partition 30 that extends transversely or orthogonally from main body portion 26. From distal wall 30 the sidewall 32 of collar 28 extends to a proximal end 34 that has an opening 36 formed concentrically with opening or cavity 38 at luer end 40 of needle hub main body portion 26. Since sidewall 32 of ring 28 is in spaced relationship with main body portion or base 26 of needle hub 4, luer end 40 of needle hub 4 accordingly is threadingly matable with a corresponding luer connector such as that shown for syringe 16 in FIG. 2.

Figure 2:
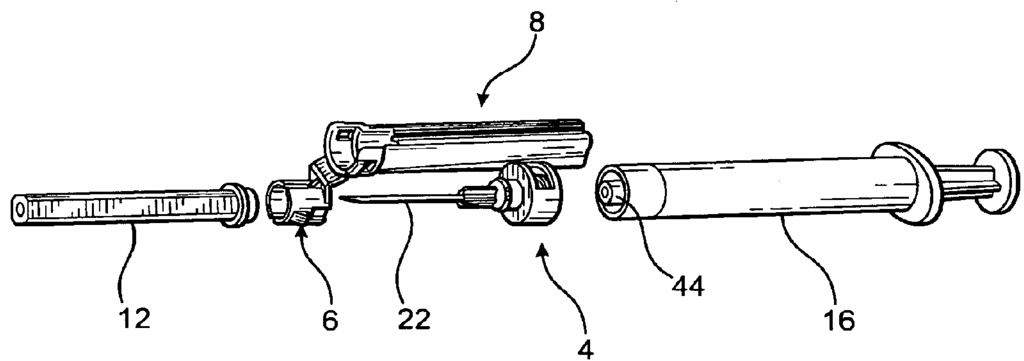
Figure 3:
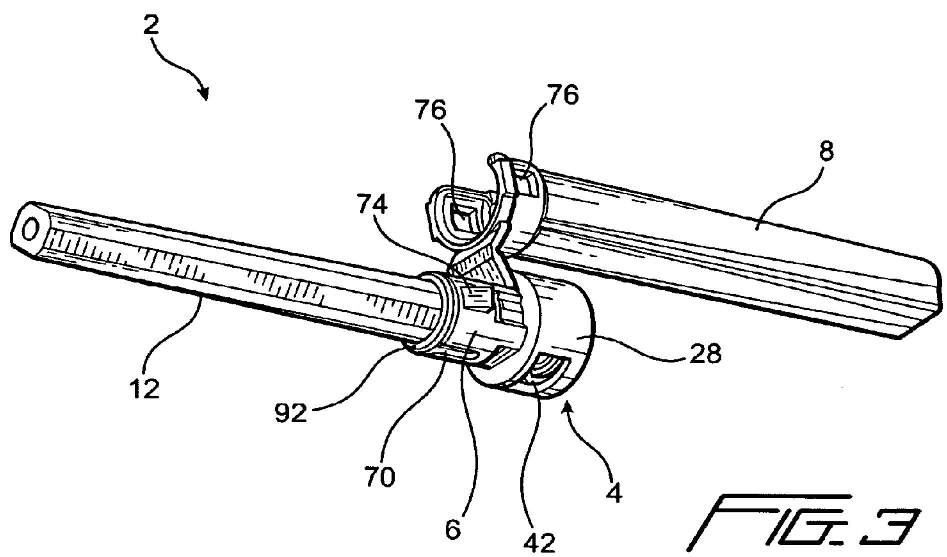
FIG. 3 is a perspective view of the safety needle assembly of the instant invention with all of the components assembled.

Ring 28 is also provided with two openings or windows 42 along its sidewall 32 to enable a user to view base portion 26 of needle hub 4. As needle hub 4, and the other components of the needle assembly, are made of conventional medical plastic such as polypropylene, or ABS plastic, and is substantially clear except for a color tinting as a way of color coding the assembly, the user can readily ascertain any flashing or blood, or blood flash, during a blood withdrawing procedure to thereby determine whether needle 22 has been correctly inserted into the vein of a patient. Thus, by way of windows 42, a user can view the base portion, as well as luer end 40 of needle hub 4. It should of course be appreciated that the safety needle assembly of the invention can also be used for infusion procedure. The dimension of ring 28 is such that it enables the user to readily grasp needle hub 4, and therefore the safety needle assembly as shown in FIG. 3, for mating to syringe 16 as shown in FIG. 2. As is well known, luer end 40 of needle hub 4 may be coupled to the corresponding luer end 44 of syringe 16 by a rotational movement when syringe 16 has a luer lock type receptacle, as shown in FIG. 2. Alternatively, in the case where the syringe has a luer slip type receptacle, the user, upon grasping ring 28, can simply insert luer 40 onto the luer slip receptacle of the syringe.

Further with respect to FIGS. 1-7 and in particular with respect to FIGS. 6 and 7, at the distal portion 20 of needle hub 4 there are provided a number of flanges 44 in a coaxially circumferential manner a predetermined distance from end wall 30 of ring 28. Flanges 44 each are chamfered or beveled at its front surface 46, and extend circumferentially proximate to the front end of cavity 38 of the base portion 26 of needle hub 4. As best shown in FIGS. 4 and 5, cavity 38 of base portion 26 is connected to needle 22 by a through bore 50 at extension 24. Extension 24 has a number of elongated ribs 56, which has no bearing for this invention other than for cosmetic and manufacturing processes not related to the instant invention, as ribs 56 do not come into contact with needle sheath 12 at any time. With flanges 44 extending from base portion 26 a predetermined distance from end wall 30, a space 52 is defined between flanges 44 and end wall 30 circumferentially about base portion 26. As best shown in FIG. 6, the back surfaces 54 of flanges 44 are formed at right angle to base portion 26.

As shown in FIGS. 1-5, needle hub 4 is in alignment with collar 6 and is coupled thereto per shown in the assembled views of FIGS. 3-5. In particular, with reference to FIGS. 8-11, collar 6 is pivotally connected to needle protection housing 8 by living hinge 10. As shown in FIG. 1, housing 8 is pivotable in the direction indicated by directional arrow 56, i.e., toward the longitudinal axis 14 for covering needle 22.

Collar 6 is cylindrical in shape and has a proximal portion or end 58 and a distal portion or end 60. There are formed at the inner surface at proximal portion 58 of collar 6 a plurality of protrusions 62 which are substantially rectangularly shaped. Protrusions 62 each may have a chamfered surface 64 that faces needle hub 4, as shown in the alignment of the components illustration of FIG. 1. Moreover, protrusion 62 are dimensioned such that when collar 6 is press-fitted to needle hub 4, they will matingly fit to space 52 defined by flanges 54 and end wall 30 at the distal portion of needle 4. The respective dimensions of space 52 and protrusions 62 may be such that, although collar 6 is rotatable about base portion 26 of needle hub 4, there nonetheless is enough friction between either one of flanges 44, end wall 30 or the outer surface of needle hub base 26 and protrusions 62 to render collar 6 not freely rotatable about needle 4, unless a predetermined torque or force is applied either to needle protection housing 8, living hinge 10 or collar 6, to rotate collar 6 relative to needle hub 4. Voids 66 provided at proximal portion 58 of collar 6 enable proximal portion 58 to flex, or expand, when collar 6 is press-fitted to the distal portion of needle hub 4, particularly when protrusions 62 come into contact with flanges 44. The respective chamfered or beveled surfaces 46 and 64 of flanges 44 and protrusions 62, respectively, facilitate the insertion of collar 6, and more particularly protrusions 62 into space 52 of needle hub 4.

Distal portion 60 of collar 6 has at its distal end, or proximate thereto, a rib 68 formed at the inner surface of collar 6. For the embodiment shown, rib 68 is divided into two halves, per notches 70 formed at opposed sides of distal portion 60. Notches 70 provide additional flexibility to the distal portion of collar 6 when needle sheath 12 is fitted thereto. More on that later. For now, it should be appreciated that rib 68 is formed to have either a semi-circular configuration or a configuration that is made up of a number of beveled surfaces for facilitating the mating of distal portion 60 of collar 6 with the proximal portion 75 of needle sheath 12. The beveled surfaces of rib 68 are collectively designated 72.

Needle protection housing 8 is connected, by living hinge 10, to collar 6 at the latter's proximal portion 58. Needle protective housing 8 has an open proximal end 75 and a closed end 78. Housing 8 is cylindrical in shape and has an opening 80 through which needle 22 passes, when housing 8 is pivoted toward collar 6 for covering needle 22 after needle sheath 12 has been removed from collar 6. Opening or channel 80 is formed by two lips or flaps 82 and 84 each of which extends longitudinally along the entire length of housing 8. Lip 82 overlaps lip 84, with the overlapping being such that the combination of lips 82 and 84 providing a trap door for needle 22. Thus, once needle 22 passes lips 82 and 84 into housing 8, it is trapped within housing 8 and is prevented from being further exposed.

Figure 10:
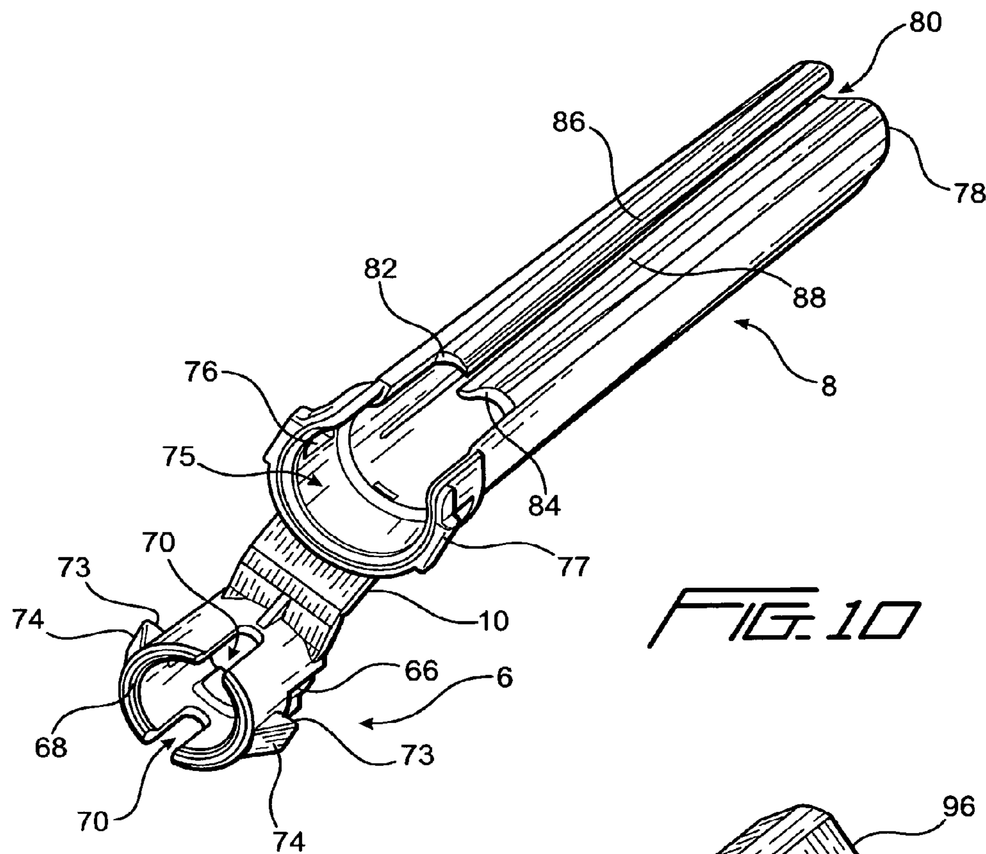
FIG. 10 is yet another view of the needle protection housing and collar of the instant invention safety needle assembly, with the lips that form the longitudinal slot along the housing clearly shown.

Opening 80, due to its formation by lips 82 and 84, is off-centered to one side of housing 8 to enhance the entry of needle 22 into housing 8. Each of lips 82 and 84 is angled, by a series of complex angles, as best shown in FIGS. 10 and 11, toward the interior of housing 8. The respective angles of each of the lips are therefore varied along the length of the housing for guiding needle 22 into housing 8 via opening 80. The respective progressively angled surfaces of lips 82 and 84 are designated 86 and 88, respectively. Given that the entry of needle 22 into housing 8 is guided by lips 82 and 84, the angled entry of needle 22 into housing 8 is effected in a smooth manner to substantially eliminate the possibility that contaminated fluid that remains on needle 22 after its use may be flickered or splattered when needle 22 comes into contact with housing 8.

To ensure that needle protection housing 8 remains fixedly retained along the longitudinal axis 14, a lock mechanism is provided at the proximal end 75 of needle housing 8 and the outer surface of collar 6. This ensures that once needle housing 8 is pivoted to the position along longitudinal axis 14, it will remain in alignment thereat. This lock mechanism, as shown in FIGS. 1-3 and 9-11, comprises two apertures 76 at the base of needle housing 8, and two corresponding one-way downward sloping catch members 74 at collar 6. Alternatively, as should readily be recognized, the apertures and catch members may be formed at collar 6 and the base of housing 8, respectively. Further, instead of apertures, non-through openings that nonetheless mate to the catch members are also envisioned. When needle protection housing 8 is pivoted to be in alignment along longitudinal axis 14, aperture 76 will snap fit over the one-way catch members 74, with the base surfaces 73 of the one-way catch members 74 acting against the top surfaces 77 at the base of apertures 76 to thereby fixedly retain needle housing 8 relative to collar 6.

Figure 12:
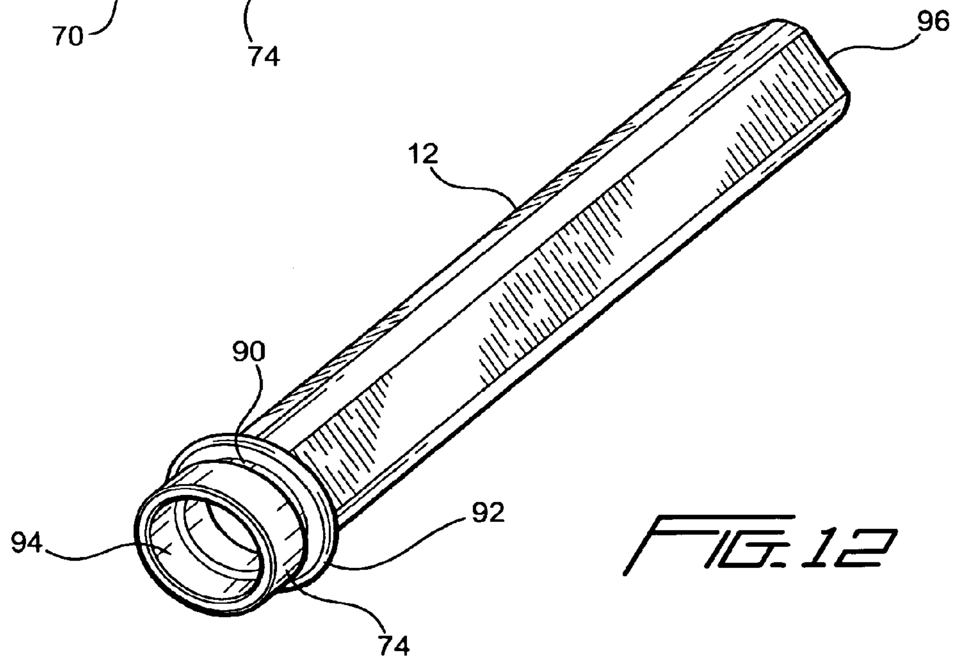
FIG. 12 is a perspective view of the needle sheath of the instant invention safety needle assembly as viewed from its open end.
Figure 13:
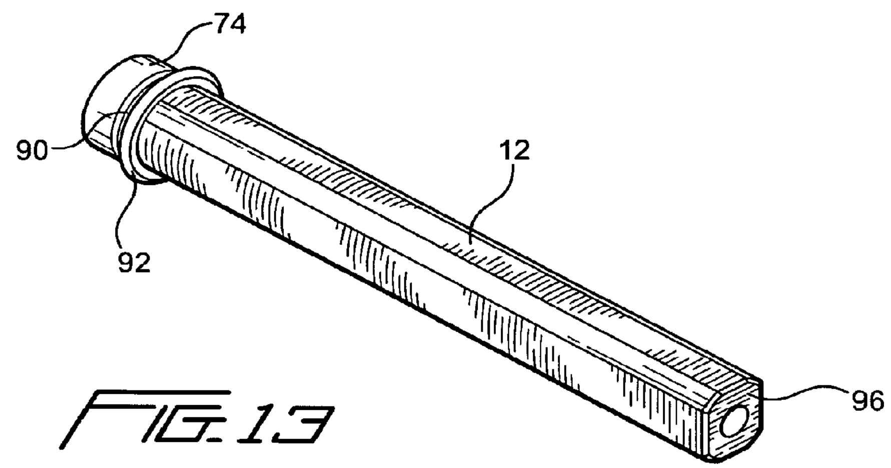
FIG. 13 is another perspective view of the needle sheath of FIG. 12 but viewed from its closed end.

As shown in FIGS. 12 and 13, needle sheath 12 has a first engage mechanism that engages to a second engage mechanism at collar 6. In particular, needle sheath 12 is a cylindrical cap that has formed at its proximal portion 75 a circumferential groove or slot 90. Groove 90 is configured to have a dimension, as defined by stop 92 and proximal portion 75, to accept rib 68 of collar 6. As shown, proximal portion 75 of needle sheath 12 has an opening 94 that allows needle sheath 12 to be placed or positioned over needle 22 and be press-fitted onto the distal end of collar 6. As the distal end of collar 6 has a rib 68 and opposed slots 70, when needle sheath 12 is fitted to collar 6, due to the elastic properties of the plastic material from which both collar 6 and needle sheath 12 are molded, the distal end of collar 6 would expand slightly so as to accept the proximal portion 75 of needle sheath 12, until rib 68 is snap fitted into groove 90, and the edge of the distal end of collar 6 rests against stop 92. Once snap fitted to collar 6, needle sheath 12 is removably engaged to collar 6. To remove needle sheath 12 from collar 6, a predetermined or greater force is applied to needle sheath 12 along longitudinal axis 14 for separating needle sheath 12 from collar 6. As best shown in FIG. 13, needle sheath 12 has a closed distal end 96.

In operation, with the assembled safety needle assembly as shown in FIG. 3, a user would remove needle sheath 12 by applying a predetermined force longitudinally relative to collar 6. Once exposed, needle 22 may be used. After use, needle protective housing 8 is pivoted to be in substantial alignment along longitudinal axis 14 so that the contaminated needle 22 enters into housing 8 and is trapped inside housing 8 by the trapdoor formed by lips 82 and 84. At the same time, housing 8 is fixedly retained to collar 6 by the mating of apertures 76 at the base of housing 8 to the one-way catch member 74 at the outer surface of collar 6. To remove needle hub 4 from the syringe, ring 28 of needle hub 4 is grasped, and in the case of a luer lock coupling, rotated counter-clockwise to remove needle hub 4 from the syringe, such as 16 shown in FIG. 2. Once removed from the syringe, the safety needle assembly could be properly disposed.

A first embodiment of the needle assembly of the instant invention is shown in FIG. 14. Elements that are the same or similar to those of the earlier embodiment are labeled the same. As shown, needle hub 4 of the FIG. 14 embodiment is the same as that shown in the earlier embodiment. Needle sheath 12, however, is a clear sheath or cap that does not come into contact with needle hub 4. In particular, needle sheath 12 is shown to have a base portion 100 that is dimensioned to have a diameter greater than the diameter of collar 6. Base portion 100 also is formed to include opposed slots or keys 102, of which only one is shown, that mate with catch members 74 (only one is shown) of collar 6. Thus, with collar 6 fitted about space or groove 52 defined between flanges 44 and end wall 30 of needle hub 4, collar 6 is rotatable about needle hub 4, when needle sheath 12 is rotated. Two opposed slits 70 are provided at the distal portion of collar 6 for providing flexibility thereat so that the needle sheath 12 can readily and tightly connect to collar 6. By being transparent, when collar 6 is seated onto groove 52 of needle hub 4 and needle sheath 12 slip-fitted over collar 6, a user can see needle 22, so as to readily determine the gauge of the needle. Once needle sheath 12 is removed from collar 6, catch members 74 would coact with the lock member apertures 76 at the base of housing 8 for fixedly retaining housing 8 to collar 6, when housing 8 is pivoted along direction 56 to cover needle 22. To connect and disconnect the needle assembly of the FIG. 14 embodiment to a syringe, the same operation as noted for the previous embodiment, namely grasping the needle hub 4, is used to rotatably connect and disconnect the same from the luer end of a syringe.

Figure 15:
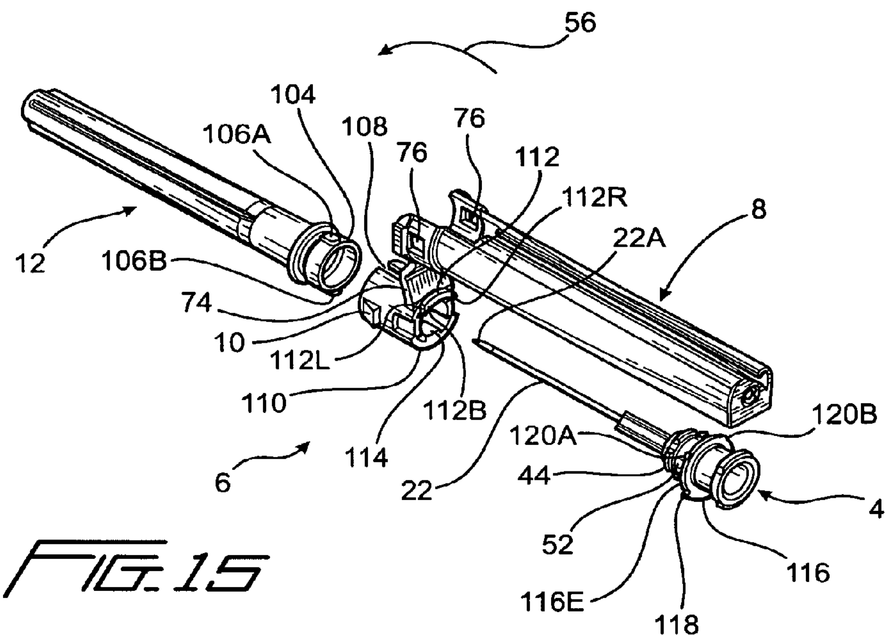
FIG. 15 is another alternative embodiment of the needle assembly of the instant invention.

The FIG. 15 embodiment of the needle assembly of the instant invention has a needle sheath having a base portion 104 that is dimensioned to fit into the distal end of collar 6. There are provided at base portion 104 of needle sheath 12 two keys 106*a* and 106*b* which are matable with corresponding slots or channels 108 (only one is shown) provided at the distal portion of collar 6. Thus, with needle sheath 12 mated to collar 6, by means of keys 106*a* and 106*b* being mated to keyways 108, collar 6 is rotatable in unison with needle sheath 12.

For the collar 6 of the FIG. 15 embodiment, there is provided at its proximal end 110 a flange 112 proximate to living hinge 10. As with the previous embodiments, there are provided within the proximal portion of collar 6 a plurality of pads 114 which are movably mounted to space or groove 52 of needle hub 4, so as to allow collar 6 to be rotatable about needle hub 4. For the FIG. 15 embodiment, a ring 116 is provided as the back end of groove 52, whereas a plurality of flanges 44 define the front end of groove 52. Ring 116 is designed to have two end stops 118 (only one being shown) that are at 180° from each other. There are also provided on the top edge of ring 116 two protuberances 120*a* and 120*b*.

With collar 6 mounted to needle hub 4, and in particular pads 114 movably resting on groove 52, the bottom surface 112*b* of flange 112 comes into contact with edge 116*e* of ring 116. With the end stops 118 at the 3 and 9 o'clock positions, collar 6 is rotatable between those end stops 118, so as to ensure that the beveled end 22*a* of needle 22 can readily be seen by the user when the user inserts needle 22 into the vein of a patient. To align housing 8 at the 12 o'clock position, collar 6 is rotated until flange 112 is positioned between protuberances 120*a* and 120*b*. Flange 112 is able to be snap-fitted between protuberances 120*a* and 120*b* due to the respective elastic characteristics of flange 112 and the protuberances, as both collar 6 and needle hub 4 are made from a conventional medical plastics material that does have a given elasticity.

With ring 116, and the interaction of flange 112 with the two end stops 118, once collar 6 is mounted to needle hub 4 and needle sheath 12 mated to collar 6, by turning needle sheath 12, assuming a clockwise movement, the left end 112*l* of flange 112 eventually comes into contract with end stop 118 to thereby cause needle hub 4 to turn when collar 6 is rotated. Similarly, when collar 6 is turned counterclockwise, (looking in the direction of needle hub 4), end 112*r* of flange 112 eventually comes into contact with the not shown end stop 118 so as to cause needle hub 4 to rotate counterclockwise.

To use the FIG. 15 needle assembly, before exposing needle 22, a user would rotate needle sheath 12 in a clockwise direction, so that collar 6, with flange 112, causes needle hub 4 to rotate in a clockwise direction to connect to a syringe. After needle sheath 12 is removed to expose needle 22, to cover needle 22, housing 8 is pivoted in the direction of arrow 56 to cover needle 22. Once needle 22 is stored within housing 8 and catch members 74 coact with lock members 76, a user could simply turn housing 8 in a counterclockwise direction so that flange 112 would abut against the not shown end stop of needle hub 4 to thereby cause needle 4 to rotated in a counterclockwise direction, thereby removing needle hub 4 and therefore the needle assembly from the syringe.

Figure 16:
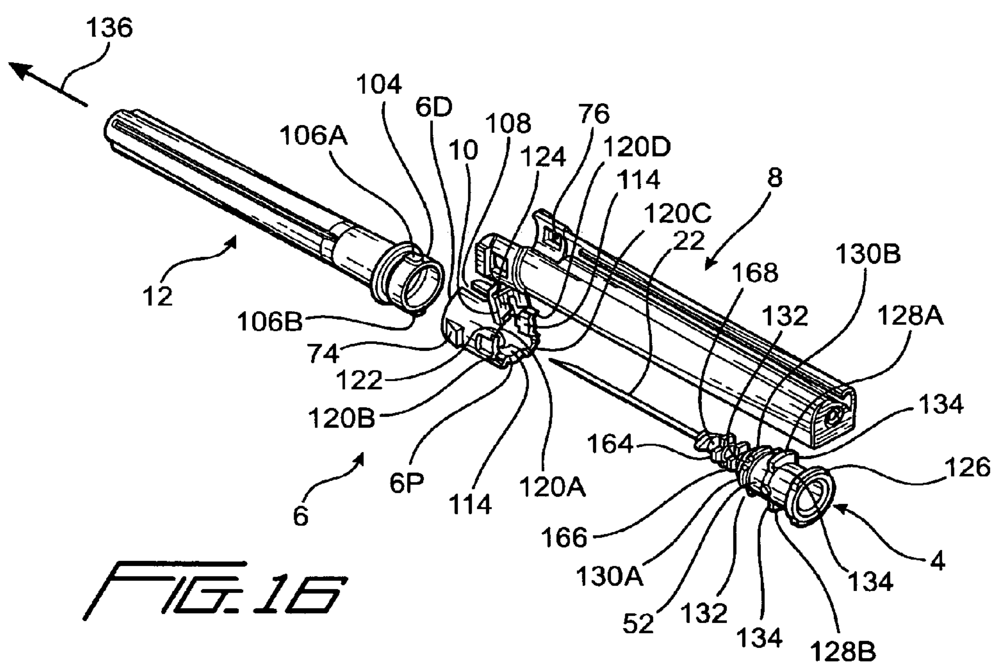
FIG. 16 is yet another alternative embodiment of the needle assembly of the instant invention.

The needle assembly of the FIG. 16 embodiment has a needle sheath 12 that is the same as that of the FIG. 15 embodiment in that it has a base portion 104 that has two opposed keys 106*a* and 106*b* at the distal end of collar 6. The collar 6 of the FIG. 16 embodiment has a proximal portion that has at the proximal end a plurality of fingers, in this instance four, designated 120*a*-120*d*. These fingers or extensions are interspersed with internal pads 114 at its proximal portion of collar 6. There is formed at each of the internal pads 114 a head or extension 122. Further with respect to collar 6, note that keyway 108 as shown extends from the distal end 6*d* of collar 6 to its proximal end 6*p* and then ends at a portion 124 of living hinge 10, which extends from the proximal portion of collar 6.

The needle hub 4 of the FIG. 16 embodiment is similar to the needle hub disclosed in the aforenoted application Ser. No. 10/649,837. In brief, needle hub 4 has a luer end 126 and two sets of flanges orthogonally extending from its main body for defining the space or groove 52 onto which internal pads 114 of collar 6 are mounted. The pair of flanges that are shown in the form of wings are designated 128*a* and 128*b* and may be referred to as the aft flanges. The other set of flanges, which may be referred to as the fore flanges, are made up of a number of adjacent flanges 130, of which only 130*a* and 130*b* are fully shown. The space defined between the adjacent flanges, for example that between flanges 130*a* and 130*b*, are designated 132.

With collar 6 rotatably mounted about needle hub 4, with internal pads 14 movably mounted on groove 52, to connect luer end 126 of needle hub 4 to a counterpart end of a syringe, a user would hold needle sheath 12, which is mated to the distal portion of collar 6, and rotate clockwise while pushing in at the same time. Due to the interlocking between keys 106 of needle sheath 12 with keyways 108 of collar 6, collar 6 is rotated in unison with needle sheath 12. By pushing needle sheath 12 toward needle hub 4, collar 6 is likewise moved forward toward needle hub 4, with corresponding pairs of fingers 120 extending between the edges of flanges 128*a* and 128*b*, designated as 134. As a consequence, when needle sheath 12 is rotated clockwise, one of the fingers 120 would come into contact with the edge of flange 128*b* while another one of the fingers 120 would come into contact with an opposite edge of flange 128*a* to thereby cause needle hub 4 to be rotated in unison with collar 6, as needle sheath 12 is being turned. The needle assembly is thus connected to a syringe.

To disconnect the needle assembly from the syringe, after the needle sheath 12 has been removed from collar 6 to expose needle 22, and with housing 8 pivoted to cover contaminated needle 22 and fixedly retained to cover 6 by the locking mechanism comprising catch members 74 at collar 6 and apertures 76 at housing 8, a user would pull housing 8 in the direction indicated by directional arrow 136 to thereby move collar 6 in a direction away from needle hub 4. When thus moved, the heads 122 extending from the internal pads 114 would eventually be fitted to the spaces 132 defined by adjacent flanges 130. Once heads 122 are caught in their respective spaces 132, by turning housing 8 in a counterclockwise direction, needle hub 4 likewise is moved in the same counterclockwise direction to thereby disconnect the needle assembly from the luer of the syringe.

Figure 17:
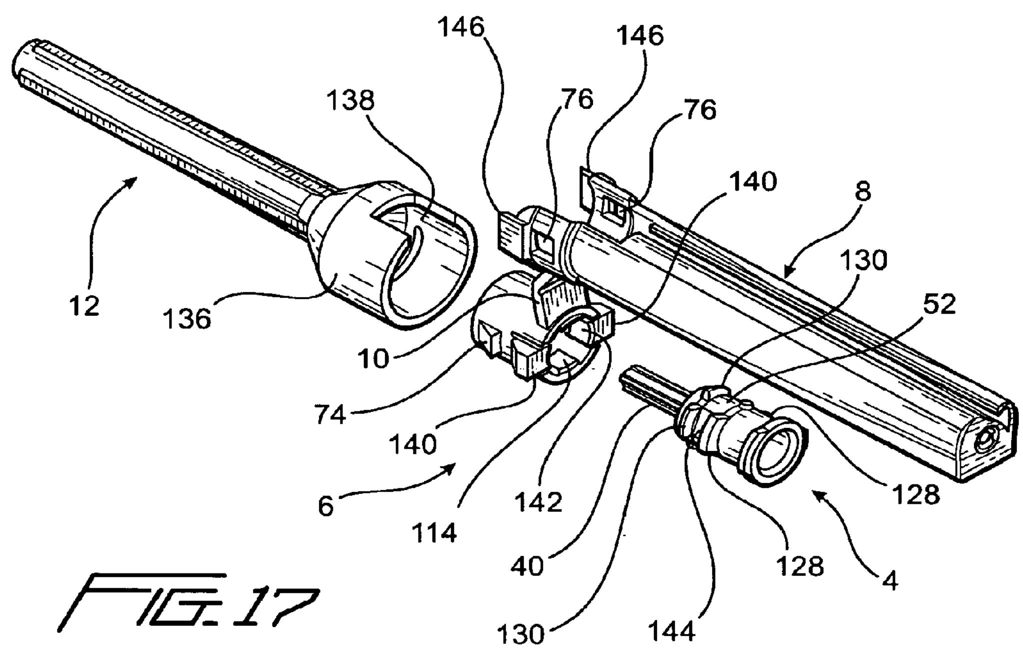
FIG. 17 is still yet another alternative embodiment of the needle assembly of the instant invention.

FIG. 17 illustrates yet another embodiment of the needle assembly of the instant invention. For the FIG. 17 embodiment, needle sheath 12 is shown to include a proximal portion 136 that has a dimension that allows it to fit over collar 6. For illustration purpose, the needle that is attached to the distal end 4*d* of the needle hub is not shown. For the FIG. 17 embodiment, needle hub 4 has a main body and, as was the case with the FIG. 16 embodiment, two sets of flanges that are orthogonally extending from the main body portion. The first set of flanges may be considered as the aft flanges 128 while the second set of flanges may be considered as the fore flanges 130.

The base portion 136 of needle sheath 12 is enlarged, with a dimension that allows it to fit over collar 6. A channel 138 is provided at portion 136 and is dimensioned to allow it to mate with the portion of living hinge 10 that extends from collar 6. Thus, for the FIG. 17 embodiment, collar 6 is substantially fitted within base portion 136 of needle sheath 12 before use.

The FIG. 17 collar 6, in addition to having the catch members 74, has connected thereto housing 8 by means of living hinge 10. Collar 6 further includes a plurality of spring arms 140, in this instance two, each having an internal pad 142 that is similar to the integral internal pad 114 at the inner wall of the proximal portion of collar 6 interspersed between the spring arms 140. As shown, each of the spring arms 140 is configured to have a bevel front end that allows portion 136 of needle sheath 12 to easily fit over. When the inner wall of portion of 136 comes into contact with the outer surface of spring arms 140, spring arms 140 are pushed inwards toward the center axis of collar 6. As spring arms 140 are pushed inwards, their respective inner pads 142 eventually come to rest when pressed against corresponding flat sections 144 (only one of which is shown) formed at groove 52 of needle hub 4. Spring arms 140, by way of their respective internal pads 142, therefore act to hold needle hub 4, when needle sheath 12 is slip fitted over collar 6. As a consequence, the needle assembly of FIG. 17 may be connected to a syringe when a user rotates needle sheath 12 in a direction, for example clockwise, that threadingly mates needle hub 4 to the luer end of a syringe.

To use, needle sheath 12 is removed with a predetermined force from collar 6. After use, to cover the contaminated needle, housing 8 is pivoted to cover the now contaminated needle, with catch members 74 of collar 6 coacting with apertures 76 of housing 8 to fixedly retain housing 8 to collar 6.

For the FIG. 17 embodiment, at the base of housing 8 adjacent to apertures 76 there are two legs or extensions that extend from the open end of housing 8. When housing 8 is pivoted to the position whereby it is in substantial alignment along the longitudinal axis of the needle for covering the needle, legs 146 would come into contact with spring arms 140 to bias spring arms 140 inwardly to again press against the corresponding flat sections 144 at needle hub 4. As a consequence, collar 6 once more fixedly holds needle hub 4 when housing 8 has been pivoted to cover the needle. At that point, to remove the needle assembly from the syringe, a user only needs to turn housing 8 in the appropriate direction, for example the counterclockwise direction, as needle hub 4 is rotated in unison with collar 6 when housing 8 is rotated.

Figure 18:
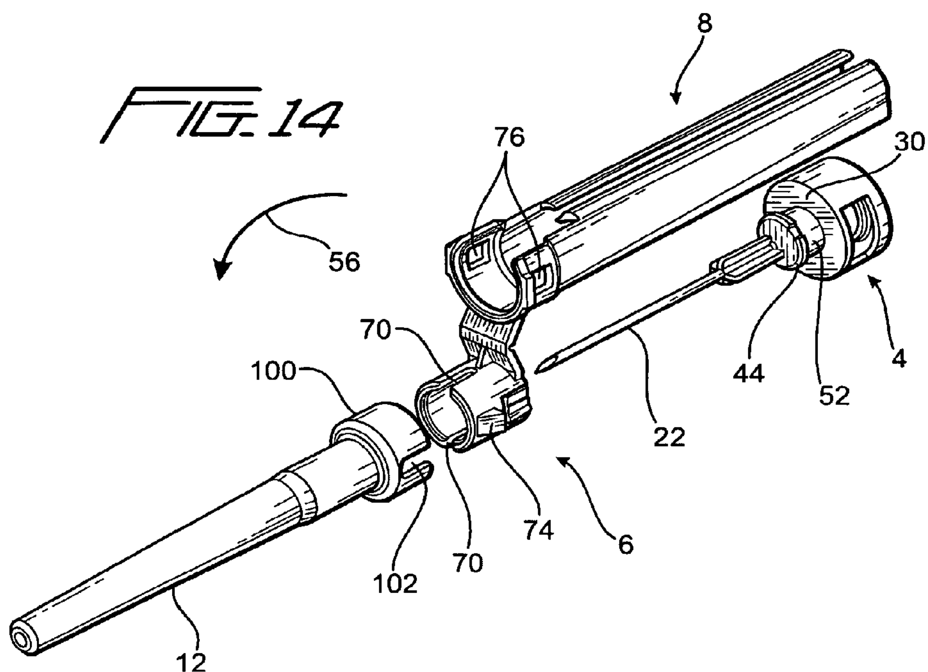
FIG. 18 is a cross-sectional view of still yet another alternative embodiment of the needle assembly of the instant invention.

FIG. 18 is a cross-sectional view of yet another embodiment of the needle assembly of the instant invention. For the FIG. 18 embodiment, needle sheath 12 has a base portion that has an opening that is dimensioned to fit into collar 6. In particular, needle sheath 12 has a contact portion 148 that fits within space 150 when needle sheath 12 is snap fitted to collar 6. Needle sheath 12 is held to collar 6 by the interaction between groove 152 and fingers 154 provided internally at the distal end of collar 6.

As shown, collar 6 has a distal portion 156 and a proximal portion 158, which has a smaller diameter than distal portion 156. There are a plurality of spring fingers 160 that extend from proximal portion 158 into the interior of distal portion 156 of collar 6. When needle sheath 12 is snap-fitted into collar 6, portion 148 thereof would bias against spring fingers 160 to force them to move toward the center of collar 6. A number of inner pads 162 provided at proximal portion 158 of collar 6 are mounted about groove 52 of needle hub 4, so that, if spring fingers 160 are left at their natural position, collar 6 is rotatable about needle hub 4.

Needle hub 4 of the FIG. 18 embodiment is the same as the needle hub shown in the FIG. 16 embodiment, which is disclosed in the aforenoted incorporated by reference application Ser. No. 10/649,837. For the FIG. 18 embodiment, there are a number of sets of concentric arms 164, 166 provided at distal portion 4*d* of needle hub 4. As best shown in FIG. 16, adjacent pairs of these arms define a V space 168 that the compressed spring fingers 160 would be engaged with, when the spring fingers 160 are pushed inward by the mating of needle sheath 12 to collar 6 in the manner as described earlier. Thus, with collar 6 rotatably mounted to needle hub 4 and needle sheath 12 snap-fitted to collar 6, the spring fingers 160 of collar 6 would fixedly hold needle hub 4, so that needle hub 4 and collar 6 would rotate in unison, when a user turns needle sheath 12, which has its portion 148 tightly and frictionally fitted within space 150 of collar 6.

As in all of the embodiments, once collar 6 is rotatably mounted to groove 52 of needle hub 4, to remove needle sheath 12, the user applies a predetermined force sufficient to separate portion 148 of needle sheath 12 from space 150 and groove 152 from fingers 154. Once needle sheath 12 is removed from collar 6, collar 6 is rotatable about needle hub 4 so that housing 8 may be positioned to a location that does not conflict with the viewing of the bevel tip of the needle. After use, to cover the contaminated needle, which for the FIG. 18 embodiment is not shown for ease of explanation, housing 8 is pivoted in the direction as shown by directional arrow 168 so that it becomes substantially in alignment along the longitudinal axis 14 of the needle assembly and be fixedly retained by the coaction of the catch members 74 of collar 6 (not shown) and apertures 76 (not shown) at housing 8.

For the FIG. 18 embodiment, housing 8 has extending at its open end a number of legs or extensions 170 that, when housing 8 is pivoted to the position in alignment with longitudinal axis 14, would enter the interior of the proximal portion 156 of collar 6, so that the extensions 170, for example extension 170*a* would fit within space 150 of collar 6 to thereby bias spring fingers 160 inwardly. Spring fingers 160 in turn would fit within one of the spaces 168 defined by adjacent arms 164 or 166, so that needle hub 4 is fixedly held to collar 6. Thus held, when a user rotates housing 8, for example in the counterclockwise direction, collar 6 is rotated in the same direction to thereby disconnect needle hub 4 from a syringe.

The invention claimed is:

1. A needle assembly, comprising:

a needle hub having a luer end and a distal portion to which a needle extends;

a collar rotatably mounted about said needle hub, said collar having a proximal end and a distal end that has at least one keyway extending from the distal end to a proximal portion of said collar;

a housing pivotally connected to said collar; and a needle sheath having an open end dimensioned to enable said needle sheath to snap fit into the distal end of said collar for covering said needle, said needle sheath having a key at its open end that mates to the keyway of said collar to interlock said sheath to said collar so that said sheath and said collar are rotatable in unison.

2. Needle assembly of claim 1, wherein said collar comprises a flange extending from its proximal end and wherein said needle hub comprises a ring, said flange being in contact with an edge of said ring when said collar is mounted to said needle hub, said ring having two end stops to limit the contact movement of said flange with said ring for preventing 360° rotation of said collar about said needle hub, said ring having at least one protrusion between the end stops to provide a guide for positioning said collar relative to said needle hub.

3. Needle assembly of claim 2, wherein said ring comprises two protrusions at the edge of said ring between the end stops, the two protrusions providing non-permanent friction guidance for said flange of said collar to enable a user to determine that said housing is positioned at 90° relative to the two end stops, the two end stops confining the rotational movement of said collar and thereby the positioning of said housing between 0° and 180° relative to said needle hub.

4. Needle assembly of claim 1, wherein said housing comprises a longitudinal slot through which said needle passes when said housing is pivoted to cover said needle, overlapping flaps each extending inwardly along the length of a corresponding edge of said slot, said flaps preventing said needle from exiting said housing once said needle has entered into said housing.

5. Needle assembly of claim 1, wherein said collar comprises a flange extending from its proximal end and wherein said needle hub comprises a ring, said flange in contact with an edge of said ring when said collar is mounted to said needle hub, said ring having two end stops for making contact with said flange so that depending on the rotational movement of said needle sheath, once said flange makes contact with either of said end stops, and depending on which of the end stops said flange makes contact with, said needle hub may be moved in either a clockwise or a counterclockwise direction for respectively connecting or disconnecting said needle hub to or from a syringe.

6. Needle assembly of claim 1, wherein the needle hub has a plurality of coplanar fore flanges and a plurality of coplanar aft flanges spaced from each other extending orthogonally from said proximal portion; and wherein said collar has a plurality of pads formed at the inner wall of said collar for rotatably anchoring said collar to said needle hub between said fore and aft flanges, a plurality of fingers extending from the proximal end of said collar adaptable to make contact with said aft flanges.

7. Needle assembly of claim 6, wherein said needle hub may be rotatably connected to a luer of a syringe by a user pushing said needle sheath and therefore said collar longitudinally toward said needle hub so that at least one of said fingers extending from the proximal end of said collar becomes engaged to a side edge of one of said aft flanges to thereby cause said needle hub to be rotated in unison with the rotation of said collar when said needle sheath is turned.

8. Needle assembly of claim 6, wherein said collar comprises at least one catch member that coacts with a lock member at said housing to fixedly retain said housing to said collar when said housing is pivoted to cover said needle after said needle sheath has been removed from said collar.

9. Needle assembly of claim 1, wherein said pads of said collar each include a head pointing toward the distal end of said collar that is adaptable to engage the side edge of one of said plurality of fore flanges, and wherein said needle hub may be rotatably disconnected from a luer end of a syringe by rotating said collar with the head of at least one of said pads being engaged to a corresponding one of said fore flanges.

10. Needle assembly of claim 9, wherein after said needle sheath has been removed to expose said needle and after said housing has been pivoted to cover said exposed needle, a user may remove the needle hub from a syringe by pulling said housing away from the syringe to cause at least one of the heads of said pads to engage one of said fore flanges to thereby enable said needle hub to rotate in unison with said housing for removal from the syringe by rotating said housing.

11. Needle assembly of claim 1, wherein the needle assembly is made of a medical plastic material having a color tinting to color code the assembly.

* * * * *